United States Patent [19]

Hayakawa et al.

[11] Patent Number: 5,110,985

[45] Date of Patent: May 5, 1992

[54] PROCESS FOR PREPARING CARBOXYALKYL-SUBSTITUTED HYDROXYLAMINE

[75] Inventors: Hiroshi Hayakawa; Kiyoshi Morimoto, both of Kanagawa, Japan

[73] Assignee: Fuji Photo Film Co., Ltd., Kanagawa, Japan

[21] Appl. No.: 612,022

[22] Filed: Nov. 9, 1990

[30] Foreign Application Priority Data

Nov. 13, 1989 [JP] Japan ................................. 1-294342

[51] Int. Cl.$^5$ ........................................... C07C 229/00
[52] U.S. Cl. ..................... 562/571; 558/390; 558/441; 562/11; 562/17; 562/43; 562/105; 562/443; 562/444; 562/448; 562/553; 562/561; 562/567; 560/38; 560/171
[58] Field of Search .................. 562/11, 17, 43, 105, 562/443, 444, 555, 561, 553, 567, 571, 448; 560/38, 171; 558/390, 441

[56] References Cited

U.S. PATENT DOCUMENTS 2,195,974  4/1940  Reppe ................................. 562/571
3,867,445  2/1975  Klemchuk .......................... 560/168

FOREIGN PATENT DOCUMENTS 0243168  10/1987  European Pat. Off. .
3324844  12/1984  Fed. Rep. of Germany ...... 562/571

OTHER PUBLICATIONS

Posner, Berichte, 38, pp. 2316–2325 (1905).
"Houben–Weyl, Methoden der Organischen Chemie," Bd X/1, pp. 1115–1116 (1971).
Sandler, "Organic Functional Group Preparations," vol. III, pp. 321–327 (1972).

*Primary Examiner*—Michael L. Shippen
*Attorney, Agent, or Firm*—Sughrue, Mion, Zinn, Macpeak & Seas

[57] ABSTRACT

A process for preparing a carboxyalkyl-substituted hydroxylamine represented by formula (I)

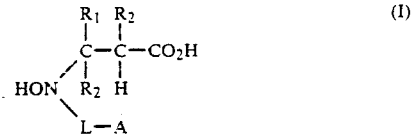

where L represents an alkylene group; A represents a hydrogen atom, a sulfo group, a carboxy group, a phosphono group, a trialkylammonio group, a hydroxy group, an amino group, an acyl group, a carbamoyl group, a sulfamoyl group, an alkoxycarbonyl group, or a cyano group; and $R_1$, $R_2$, and $R_3$, which may be the same or different, each represent a hydrogen atom, an alkyl group, or an aryl group; which comprises: reacting an α,β-unsaturated carboxylic acid represented by formula (II) as an alkylating agent

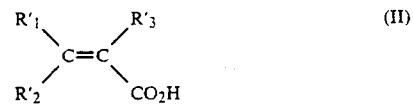

where $R'_1$, $R'_2$, and $R'_3$, which may be the same or different, each represent the same group as defined for $R_1$, $R_2$, and $R_3$, with a hydroxylamine of the formula HO—NH—R", where R" represents a hydrogen atom or an alkyl group which may be substituted with a sulfo group, a carboxy group, a phosphono group, a trialkylammonio group, a hydroxy group, an amino group, an acyl group, a carbamoyl group, a sulfamoyl group, an alkoxycarbonyl group, or a cyano group, in the presence of a solvent comprising: (a): (i) an organic polar solvent alone or (ii) a solvent mixture of water and an organic polar solvent when A is a sulfo group, a carboxy group, a phosphono group, or a trialkylammonio group; or (b): (i) water alone, (ii) an organic polar solvent alone, or (iii) a solvent mixture of water with an organic polar solvent when A is a hydrogen atom, a hydroxy group, an amino group, an acyl carbamoyl group, a sulfamoyl group, an alkoxy group, or a cyano group.

9 Claims, No Drawings 5,110,985

PROCESS FOR PREPARING CARBOXYALKYL-SUBSTITUTED HYDROXYLAMINE

FIELD OF THE INVENTION

This invention relates to a process for preparing a carboxyalkyl-substituted hydroxylamine which is useful for processing solutions for photography.

BACKGROUND OF THE INVENTION

There are only two known carboxyalkyl-substituted hydroxylamine compounds represented by formula (I) shown below.

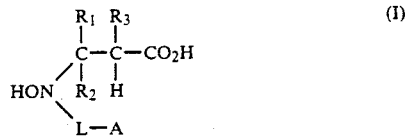

where L represents an alkylene group; A represents a hydrogen atom, a sulfo group, a carboxy group, a phosphono group, a trialkylammonio group, a hydroxy group, an amino group, an acyl group, a carbamoyl group, a sulfamoyl group, an alkoxycarbonyl group, or a cyano group; and $R_1$, $R_2$, and $R_3$, which may be the same or different, each represent a hydrogen atom, an alkyl group, or an aryl group. These are compounds (III) and (IV). Their synthesis is described in the *Tetrahedron Letters* 3027-30 (1975) and German Patent 1,159,634 respectively:

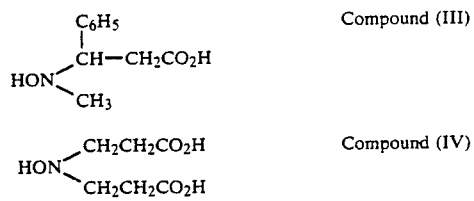

Compound (III) is synthesized according to the two step process shown in reaction scheme (a):

Reaction scheme (a)

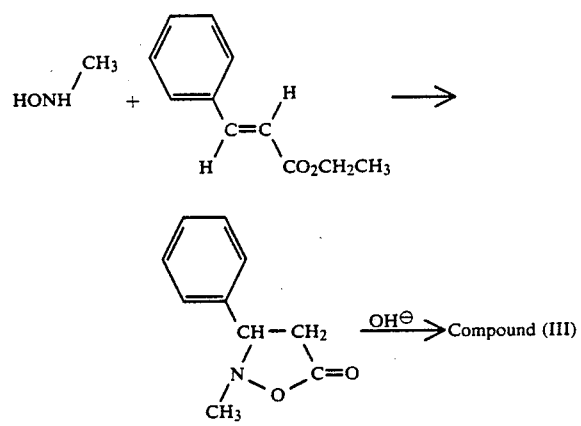

The disadvantage of this synthesis process is that it requires two steps; a single step process would be preferrable.

The synthetic method of compound (IV) is described in German patent 1,159,634. This patent describes how compound (IV) is precipitated from the reaction mixture according to reaction scheme (b). However, an attempt to produce compound (IV) according to reaction scheme (b) did not yield compound (IV), but rather the following, compound (V) precipitated as crystals from the reaction mixture.

Reaction scheme (b)

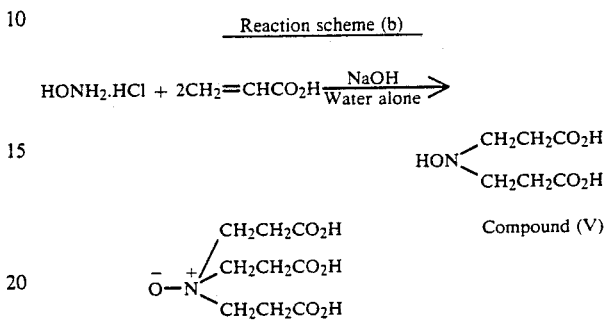

The formation ratio of compound (IV) to compound (V) in the reaction mixture was determined by NMR and found to be 17:83. Thus, compound (V) was formed as the main product, and the crystals of only compound (V) formed.

According to the method described in German Patent 1,159,634, compound (IV) can be prepared only as a by-product of the production of compound (V). Thus, this in not a technique for preparing compound (IV) at a high yield.

In order to use carboxyalkyl-substituted hydroxylamines represented by formula (I) described below, for processing solutions for photography, for example, a process is desired by which these compounds can be easily and directly prepared and by-products such as the compound (V) are avoided.

SUMMARY OF THE INVENTION

One object of the present invention is to provide a method that is simpler and more direct than the currently known methods described above.

This and other objects of the invention are satisfied by a process for preparing a carboxyalkyl-substituted hydroxylamine represented by formula (I):

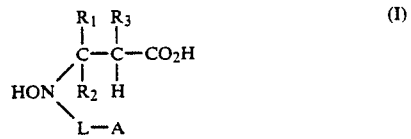

where L represents an alkylene group; A represents a hydrogen atom, a sulfo group, a carboxy group, a phosphono group, a trialkylammonio group, a hydroxy group, an amino group, an acyl group, a carbamoyl group, a sulfamoyl group, an alkoxycarbonyl group, or a cyano group; and $R_1$, $R_2$ and $R_3$ which may be the same or different, each represent a hydrogen atom, an alkyl group, or an aryl group, comprising reacting an α,β-unsaturated carboxylic acid represented by formula (II) as an alkylating agent:

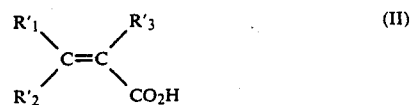

where $R'_1$, $R'_2$, and $R'_3$, which may be the same or different, each represent the same group as defined for $R_1$, $R_2$, and $R_3$, with a hydroxylamine of the formula HO—NH—R″, where R″ represents a hydrogen atom or an alkyl group which may be substituted with a sulfo group, a carboxy group, a phosphono group, a trialkylammonio group, a hydroxy group, an amino group, an acyl group, a carbamoyl group, a sulfamoyl group, an alkoxycarbonyl group, or a cyano group, in the presence of a solvent comprising: (a): (i) an organic polar solvent alone or (ii) a solvent mixture of water and an organic polar solvent when A is a sulfo group, a carboxy group, a phosphono group, or a trialkylammonio group; or (b): (i) water alone, (ii) an organic polar solvent alone, or (iii) a solvent mixture of water with an organic polar solvent when A is a hydrogen atom, a hydroxy group, an amino group, an acyl group, a carbamoyl group, a sulfamoyl group, an alkoxy group, or a cyano group.

DETAILED DESCRIPTION OF THE INVENTION

When carboxyalkyl-substituted hydroxylamine represented by formula (I) is synthesized and A is an anionic or cationic hydrophilic group chosen from the group consisting of a sulfo group, a phosphono group, a carboxy group, or a trialkylammonio group, if water is used as the reaction solvent, by-products such as the above-mentioned compound (V) are formed, and substantially no carboxyalkyl-substituted hydroxylamine, the desired product, can be isolated.

When an organic polar solvent alone or a solvent mixture of water with an organic polar solvent as described in the invention is used as the reaction solvent, the formation of by-products such as the compound (V) is suppressed. Then, carboxyalkyl-substituted hydroxylamines are formed as the main product that can be isolated with a good yield.

In the case when A is a substituent other than a sulfo group, a phosphono group, a carboxy group, or a trialkylammonio group, carboxyalkyl-substituted hydroxyamines can be synthesized and isolated using either water alone, an organic polar solvent alone, or a solvent mixture of water with an organic polar solvent. Thus, by using water alone, an organic polar solvent alone, or a solvent mixture of water with an organic polar solvent, depending on the hydroxylamine that is the reaction substrate, it has unexpectedly been found that the formation ratio of the desired product is dramatically improved. This permits a high yield synthesis of a carboxyalkyl-substituted hydroxylamine represented by formula (I).

In contrast, when a β-halopropionic acid derivative represented by formula (VI) is used as the alkylating agent, the progress of its reaction with a hydroxlamine is slow, many by-products are formed, and the yield of the desired product is very low.

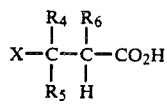

In formula (VI) X represents a halogen atom; and $R_4$, $R_5$, and $R_6$, which may be the same or different, each represent a hydrogen atom, an alkyl group, or an aryl group.

To prepare a carboxyalkyl-substituted hydroxylamine represented by formula (I), it is necessary to selectively synthesize the desired product by suppressing formation of by-products such as the compound (V). Accordingly, the synthetic conditions of the present invention are achieved by using an α,β-unsaturated carboxylic acid represented by the formula (II) as the alkylating agent, and using water alone, an organic polar solvent alone, or a solvent mixture of water with an organic polar solvent. The solvent chosen depends on the hydroxylamine that is the reaction substrate.

Compounds represented by formulae (I) and (II) of the present invention are described in detail below.

L represents an alkylene group which may be substituted such as straight or branched alkylene groups having 1 to 10 carbon atoms which may be also substituted; preferably these groups have 1 to 5 carbon atoms. Examples of these substituent groups are a hydroxy group, a carboxy group, and an aryl group. A is preferably a hydrogen atom, a sulfo group, a carboxy group, a phosphono group, a trialkylammonio group, a hydroxy, or an amino group. $R_1$, $R_2$, and $R_3$ may be the same or different and each represent a hydrogen atom, a substituted or unsubstituted $C_{1-10}$ alkyl group, or a substituted or unsubstituted $C_{6-10}$ aryl group. Preferred examples of $R_1$, $R_2$, and $R_3$ are a hydrogen atom, an alkyl group having 1 to 3 carbon atoms, or a phenyl group.

The total carbon number of —L—A in formula (I) or R″ in the hydroxylamine is up to 15.

When the alkyl group or phenyl group of $R_1$, $R_2$ and $R_3$ is further substituted, examples of these substituents are a hydroxy group, a carboxy group, a sulfo group, or a phosphono group.

The following are specific non-limiting examples of carboxyalkyl-substituted hydroxylamines represented by formula (I) that can be synthesized according to the method of the present invention.

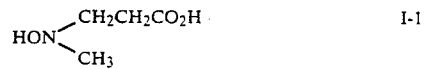 I-1

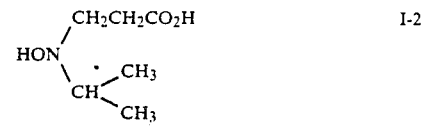 I-2

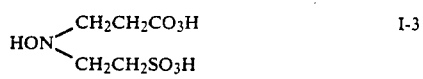 I-3

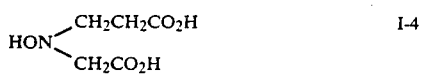 I-4

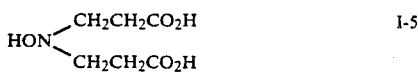 I-5

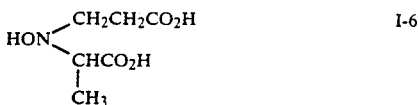 I-6

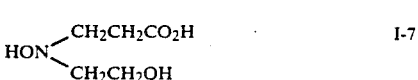 I-7

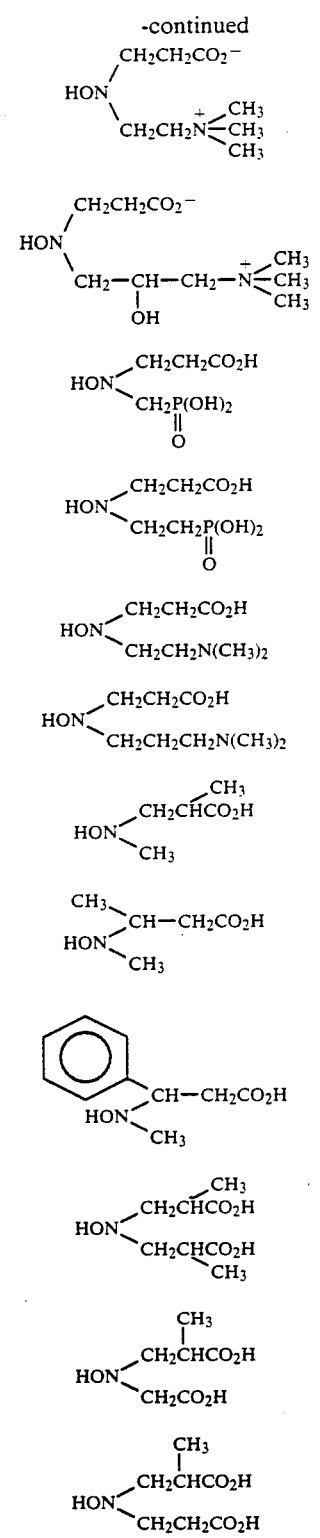

The following are specific non-limiting examples of α,β-unsaturated carboxylic acids represented by formula (II) that may be used in the present invention.

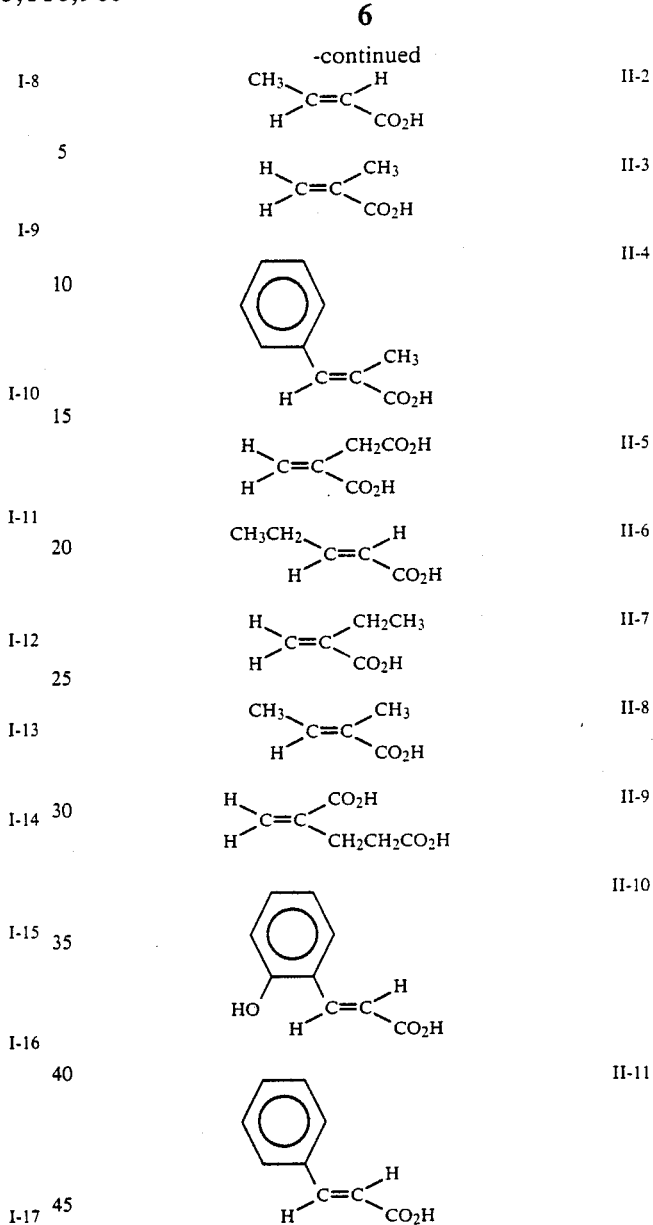

When the starting hydroxylamines of the formula HO—NH—R″ are in the form of hydrochlorides or sulfates, they are preferably neutralized with an appropriate base (e.g., sodium hydroxide, sodium carbonate, or triethylamine, pyridine).

The amount of the base used to neutralize the α,β-unsaturated carboxylic acid is preferably 0 to 1-time mole of the α,β-unsaturated carboxylic acid, more preferably 0.3 to 1-time mole. Examples of base that can be used are sodium hydroxide, potassium hydroxide, lithium hydroxide, sodium carbonate, potassium carbonate, sodium hydrogen carbonate, potassium hydrogen carbonate, triethylamine, and pyridine. The amount of the α,β-unsaturated carboxylic acid employed is preferably 0.5 to 2.5-time moles of the hydroxylamines, more preferably 0.7 to 2.2-time moles.

The reaction solvent employed may be water alone, an organic polar solvent alone, or a solvent mixture of water with an organic polar solvent.

The organic polar solvent is preferably methanol, ethanol, isopropyl alcohol, n-propyl alcohol, n-butyl alcohol, diethyl ether, tetrahydrofuran, or N,N-dimethylformamide; more preferably methanol, ethanol, or isopropyl alcohol.

When water and an organic polar solvent are used as a mixture, it is preferable to add 0 to 4-time volumes of water relative to the volume of the organic polar solvent.

The reaction temperature may be in the range of from 0° to 100° C., preferably from 10° to 90° C. The progress of the reaction can be examined using a variety of analytical means such as by NMR.

The product can be isolated as an alkali metal (such as sodium or potassium) salt of the carboxylic acid, or as a betaine.

The present invention is now described in further detail in the following, non-limiting Examples. Unless otherwise indicated, all ratios and percentages are by weight.

EXAMPLE 1

A di-substituted hydroxylamine was synthesized according to the following reaction scheme:

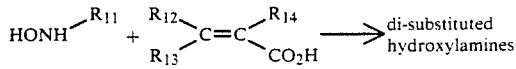

where $R_{11}$ to $R_{14}$ are as set forth in Table 1 below.

Synthesis was carried out by adding a hydroxylamine to a solvent, and also adding, if necessary, a base (see Table 1). Subsequently, an $\alpha,\beta$-unsaturated carboxylic acid was slowly added. After the reaction was completed, the reaction mixture was adjusted to pH 4 to 5 with an acid, and left to stand at room temperature to give the desired product as crystals. The results are shown in Table 1.

Table 1 shows that the indicated carboxyalkyl-substituted hydroxylamines represented by the formula (I) were prepared with good yield.

TABLE I

| No. | Exemplary compound | Hydroxylamine | $\alpha,\beta$-unsaturated carboxylic acid | Reaction solvent | Base | Reaction temperature Reaction time | Isolation yield | Remarks |
|---|---|---|---|---|---|---|---|---|
| 1 | (4) | $R_{11} = CH_2CO_2H$ 0.1 mol | $R_{12} = R_{13} = R_{14} = H$ 0.1 mol | Water 100 ml | NaOH 0.2 mol | 25° C. 3 hours | 8% | Comparative example |
| 2 | (5) | $R_{11} = CH_2CH_2CO_2H$ 0.1 mol | $R_{12} = R_{13} = R_{14} = H$ 0.1 mol | Water 100 ml | NaOH 0.2 mol | " | 7% | Comparative example |
| 3 | (3) | $R_{11} = CH_2CH_2SO_3H$ 0.1 mol | $R_{12} = R_{13} = R_{14} = H$ 0.1 mol | Water 100 ml | NaOH 0.2 mol | " | 10% | Comparative example |
| 4 | (10) | $R_{11} = CH_2\overset{O}{\underset{\|}{P}}(OH)_2$ 0.1 mol | $R_{12} = R_{13} = R_{14} = H$ 0.1 mol | Water 100 ml | NaOH 0.3 mol | " | 9% | Comparative example |
| 5 | (8) | $R_{11} = CH_2CH_2\overset{+}{N}(CH_3)_3Cl^-$ 0.1 mol | $R_{12} = R_{13} = R_{14} = H$ 0.1 mol | Water 100 ml | NaOH 0.1 mol | " | 11% | Comparative example |
| 6 | (4) | $R_{11} = CH_2CO_2H$ 0.1 mol | $R_{12} = R_{13} = R_{14} = H$ 0.1 mol | Methanol 100 ml | Triethylamine 0.2 mol | " | 75% | Present invention |
| 7 | (5) | $R_{11} = CH_2CH_2CO_2H$ 0.1 mol | $R_{12} = R_{13} = R_{14} = H$ 0.1 mol | Methanol 100 ml | Triethylamine 0.2 mol | " | 79% | Present invention |
| 8 | (3) | $R_{11} = CH_2CH_2SO_3H$ 0.1 mol | $R_{12} = R_{13} = R_{14} = H$ 0.1 mol | Methanol 100 ml | Triethylamine 0.2 mol | " | 81% | Present invention |
| 9 | (10) | $R_{11} = CH_2\overset{O}{\underset{\|}{P}}(OH)_2$ 0.1 mol | $R_{12} = R_{13} = R_{14} = H$ 0.1 mol | Methanol 100 ml | Triethylamine 0.3 mol | " | 77% | Present invention |
| 10 | (8) | $R_{11} = CH_2CH_2\overset{+}{N}(CH_3)_3Cl^-$ 0.1 mol | $R_{12} = R_{13} = R_{14} = H$ 0.1 mol | Methanol 100 ml | Triethylamine 0.1 mol | " | 82% | Present invention |
| 11 | (4) | $R_{11} = CH_2CO_2H$ 0.1 mol | $R_{12} = R_{13} = R_{14} = H$ 0.1 mol | Methanol 50 ml Water 50 ml | Triethylamine 0.2 mol | 25° C. 3 hours | 65% | Present invention |
| 12 | " | $R_{11} = CH_2CO_2H$ 0.1 mol | $R_{12} = R_{13} = R_{14} = H$ 0.1 mol | Ethanol 100 ml | Triethylamine 0.2 mol | " | 81% | Present invention |
| 13 | " | $R_{11} = CH_2CO_2H$ 0.1 mol | $R_{12} = R_{13} = R_{14} = H$ 0.1 mol | Isopropyl alcohol 100 ml | Triethylamine 0.2 mol | " | 87% | Present invention |
| 14 | " | $R_{11} = CH_2CO_2H$ 0.1 mol | $R_{12} = R_{13} = R_{14} = H$ 0.1 mol | Isopropyl alcohol 50 ml Water 50 ml | Triethylamine 0.2 mol | " | 83% | Present invention |
| 15 | (1) | $R_{11} = CH_3$ 0.1 mol | $R_{12} = R_{13} = R_{14} = H$ 0.1 mol | Water 100 ml | NaOH 0.1 mol | " | 39% | Present invention |

TABLE I-continued

| No. | Exemplary compound | Hydroxylamine | α,β-unsaturated carboxylic acid | Reaction solvent | Base | Reaction temperature Reaction time | Isolation yield | Remarks |
|---|---|---|---|---|---|---|---|---|
| 16 | (7) | $R_{11}$ = CH$_2$CH$_2$OH 0.1 mol | $R_{12}$ = $R_{13}$ = $R_{14}$ = H 0.1 mol | Water 100 ml | NaOH 0.1 mol | " | 35% | Present invention |
| 17 | (13) | $R_{11}$ = CH$_2$CH$_2$CH$_2$N(CH$_3$)$_2$ 0.1 mol | $R_{12}$ = $R_{13}$ = $R_{14}$ = H 0.1 mol | Methanol 50 ml Water 50 ml | Triethylamine 0.1 mol | " | 62% | Present invention |
| 18 | (1) | $R_{11}$ = CH$_3$ 0.1 mol | $R_{12}$ = $R_{13}$ = $R_{14}$ = H 0.1 mol | Methanol 100 ml | Triethylamine 0.1 mol | " | 83% | Present invention |
| 19 | (1) | $R_{11}$ = CH$_3$ 0.1 mol | $R_{12}$ = $R_{13}$ = $R_{14}$ = H 0.1 mol | Methanol 50 ml Water 50 ml | Triethylamine 0.1 mol | 25° C. 3 hours | 65% | Present invention |
| 20 | (16) | $R_{11}$ = CH$_3$ 0.1 mol | $R_{12}$ = C$_6$H$_5$, $R_{13}$, $R_{14}$ = H 0.1 mol | Isopropyl alcohol 100 ml | Triethylamine 0.1 mol | " | 85% | Present invention |
| 21 | (5) | $R_{11}$ = H 0.1 mol | $R_{12}$ = $R_{13}$ = $R_{14}$ = H 0.2 mol | Methanol 100 ml | Triethylamine 0.1 mol | " | 81% | Present invention |
| 22 | (17) | $R_{11}$ = H 0.1 mol | $R_{12}$ = $R_{13}$ = H$_1$, $R_4$ = CH$_3$ 0.2 mol | Methanol 20 ml Water 80 ml | NaOH 0.2 mol | 30° C. 4 hours | 58% | Present invention |
| 23 | (5) | $R_{11}$ = H 0.1 mol | $R_{12}$ = $R_{13}$ = $R_{14}$ = H 0.2 mol | Water 200 ml | None | 35° C. 3 hours | 7% | Comparative example (the synthetic method according to the method of West German Patent No. 1,159,634.) |

According to the method of the present invention, carboxyalkyl-substituted hydroxylamines can easily be synthesized from readily available starting materials, and from these hydroxylamines it is possible to prepare a variety of useful compounds to enhance the utilization and value of processing liquors in photography and related arts.

While the invention has been described in detail and with reference to specific embodiments thereof, it will be apparent to one skilled in the art that various changes and modifications can be made therein without departing from the spirit and scope of the invention.

What is claimed is:

1. A process for preparing a carboxyalkyl-substituted hydroxylamine represented by formula (I):

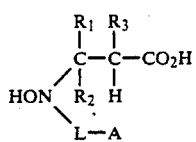
(I)

where L represents an alkylene group; A represents a hydrogen atom, a sulfo group, a carboxy group, a phosphono group, a trialkylammonio group, a hydroxy group, an amino group, an acyl group, a carbamoyl group, a sulfamoyl group, an alkoxycarbonyl group, or a cyano group; and $R_1$, $R_2$, and $R_3$, which may be the same or different, each represent a hydrogen atom, an alkyl group, or an aryl group; said process comprising the step of, reacting an α,β-unsaturated carboxylic acid represented by formula (II) as an alkylating agent:

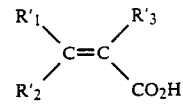
(II)

where $R'_1$, $R'_2$, and $R'_3$, which may be the same or different, each represent the same group as defined for $R_1$, $R_2$, and $R_3$, with a hydroxylamine of the formula HO—NH—R", where R" represents a hydrogen atom or an alkyl group which may be substituted with a sulfo group, a carboxy group, a phosphono group, a trialkylammonio group, a hydroxy group, an amino group, an acyl group, a carbamoyl group, a sulfamoyl group, an alkoxycarbonyl group, or a cyano group, in the presence of a solvent comprising:

(a): (i) an organic polar solvent alone or
(ii) a solvent mixture of water and an organic polar solvent
when A is a sulfo group, a phosphono group, a carboxy group, or a trialkylammonio group; or (b): (i) water alone,
(ii) an organic polar solvent alone, or
(iii) a solvent mixture of water with an organic polar solvent
when A is a hydrogen atom, a hydroxy group, an amino group, an acyl group, a carbamoyl group, a sulfamoyl group, an alkoxycarbonyl group, or a cyano group, wherein the α,β-unsaturated carboxylic acid has been neutralized by a base in the amount 0.3 to 1 mole per mole of the α,β-unsaturated carboxylic acid.

2. A process for preparing a carboxyalkyl-substituted hydroxylamine as claimed in claim 1, wherein said reacting step takes place at from 10° to 90° C.

3. A process for preparing a carboxyalkyl-substituted hydroxylamine as claimed in claim 1, wherein L is a straight or branched alkylene group having 1–10 carbon atoms.

4. A process for preparing a carboxyalkyl-substituted hydroxylamine as claimed in claim 3, wherein said straight or branched alkylene group is substituted with a hydroxy group, a carboxy group, or an aryl group.

5. A process for preparing a carboxyalkyl-substituted hydroxylamine as claimed in claim 1, wherein A is a hydrogen atom, a sulfo group, a carboxy group, a phosphono group, a trialkylammonio group, a hydroxy group, or an amino group.

6. A process for preparing a carboxyalkyl-substituted hydroxylamine as claimed in claim 1, wherein $R_1$, $R_2$, and $R_3$, which may be the same or different, each represent a hydrogen atom, an alkyl group having 1–3 carbon atoms, or a phenyl group.

7. A process for preparing a carboxyalkyl-substituted hydroxylamine as claimed in claim 1, wherein the base is sodium hydroxide, potassium hydroxide, lithium hydroxide, sodium carbonate, potassium carbonate, sodium hydrogen carbonate, potassium hydrogen carbonate, triethylamine, or pyridine.

8. A process for preparing a carboxyalkyl-substituted hydroxylamine as claimed in claim 7, wherein the reaction time is from 3 to 4 hours.

9. A process for preparing a carboxyalkyl-substituted hydroxylamine as claimed in claim 1, wherein the reaction time is from 3 to 4 hours.

* * * * *